United States Patent
Guzman et al.

(10) Patent No.: US 12,251,584 B2
(45) Date of Patent: Mar. 18, 2025

(54) PERSONAL CARE COMPOSITIONS

(71) Applicant: Colgate-Palmolive Company, New York, NY (US)

(72) Inventors: Abigail Guzman, Mexico City (MX); Sharon Kennedy, Randallstown, MD (US); Juan Mauricio Mora-Pale, Mexico City (MX); Sarita Vera Mello, Ringwood, NJ (US)

(73) Assignee: Colgate-Palmolive Company, New York, NY (US)

( * ) Notice: Subject to any disclaimer, the term of this patent is extended or adjusted under 35 U.S.C. 154(b) by 56 days.

(21) Appl. No.: 17/902,805

(22) Filed: Sep. 3, 2022

(65) Prior Publication Data

US 2023/0082090 A1 Mar. 16, 2023

Related U.S. Application Data

(60) Provisional application No. 63/260,875, filed on Sep. 3, 2021.

(51) Int. Cl.
*A61Q 15/00* (2006.01)
*A61K 8/34* (2006.01)
*A61K 8/81* (2006.01)
*A61K 8/86* (2006.01)

(52) U.S. Cl.
CPC .............. *A61Q 15/00* (2013.01); *A61K 8/345* (2013.01); *A61K 8/8152* (2013.01); *A61K 8/86* (2013.01); *A61K 2800/48* (2013.01)

(58) Field of Classification Search
CPC ........ A61K 8/86; A61K 8/8152; A61K 8/345; A61K 2800/48; A61Q 15/00
See application file for complete search history.

(56) References Cited

U.S. PATENT DOCUMENTS

| | | | |
|---|---|---|---|
| 2,350,047 A * | 5/1944 | Klarmann | A61K 8/26 424/68 |
| 5,262,153 A | 11/1993 | Mishima et al. | |
| 5,618,522 A | 4/1997 | Deckner et al. | |
| 5,785,962 A | 7/1998 | Hinz et al. | |
| 6,017,548 A | 1/2000 | Epstein et al. | |
| 6,139,850 A | 10/2000 | Hahn et al. | |
| 6,365,137 B1 | 4/2002 | Aust et al. | |
| 7,250,174 B2 | 7/2007 | Lee et al. | |
| 8,227,426 B2 | 7/2012 | Gupta et al. | |
| 8,435,955 B2 | 5/2013 | Masui et al. | |
| 8,673,327 B2 | 3/2014 | Lemoine et al. | |
| 8,741,357 B2 | 6/2014 | Lamy et al. | |
| 8,802,065 B2 | 8/2014 | Oshimura et al. | |
| 8,933,131 B2 | 1/2015 | Carter et al. | |
| 8,992,898 B2 | 3/2015 | Klingman | |
| 9,566,223 B2 | 2/2017 | Klingman | |
| 9,713,604 B2 | 7/2017 | Dreher | |
| 10,071,103 B2 | 9/2018 | Sengupta et al. | |
| 10,406,085 B2 | 9/2019 | Dubovoy et al. | |
| 10,532,014 B2 | 1/2020 | Lesniak et al. | |
| 10,561,593 B2 | 2/2020 | Wu | |
| 10,638,755 B2 | 5/2020 | Pesaro et al. | |
| 10,864,147 B2 | 12/2020 | Hilliard, Jr. et al. | |
| 10,933,000 B2 | 3/2021 | Hilliard, Jr. et al. | |
| 11,090,249 B2 | 8/2021 | Mitchell et al. | |
| 11,104,868 B2 | 8/2021 | Hardy et al. | |
| 2003/0053970 A1 | 3/2003 | Bruening et al. | |
| 2004/0076654 A1 | 4/2004 | Vinson et al. | |
| 2006/0182708 A1* | 8/2006 | Bockmuhl | A61K 36/25 424/770 |
| 2007/0167529 A1 | 7/2007 | Walton et al. | |
| 2007/0243155 A1* | 10/2007 | Bottiglieri | A61K 8/9794 424/74 |
| 2008/0187562 A1 | 8/2008 | Fan et al. | |
| 2008/0206170 A1 | 8/2008 | Nivaggioli et al. | |
| 2008/0299068 A1* | 12/2008 | Omura | A61P 43/00 424/78.08 |
| 2010/0189753 A1 | 7/2010 | Van Bavel et al. | |
| 2012/0006348 A1 | 1/2012 | Grollier et al. | |
| 2013/0059929 A1 | 3/2013 | Koehler et al. | |
| 2014/0205555 A1 | 7/2014 | Gale et al. | |
| 2015/0050227 A1 | 2/2015 | Liu et al. | |
| 2015/0202136 A1 | 7/2015 | Lanzalaco et al. | |
| 2016/0151257 A1 | 6/2016 | Klingman | |
| 2017/0183452 A1 | 6/2017 | Panandiker et al. | |
| 2018/0177692 A1 | 6/2018 | Garcia et al. | |
| 2019/0183780 A1 | 6/2019 | Pan et al. | |
| 2019/0270951 A1 | 9/2019 | Hardy et al. | |
| 2020/0016053 A1 | 1/2020 | Hilliard, Jr. et al. | |

(Continued)

FOREIGN PATENT DOCUMENTS

| CN | 101107045 | 1/2008 |
|---|---|---|
| CN | 101182299 | 5/2008 |

(Continued)

OTHER PUBLICATIONS

Colgate-Palmolive, 2021, "Atopicare Shower Cream", Mintel Database GNPD AN: 8747223.
Institut Esthederm, 2011, "E.V.E. Essential Vital Elements Serum Source", Mintel Database GNPD AN: 1666406.
International Search Report and the Written Opinion of the International Searching Authority issued in International Application PCT/US2022/042327 mailed Dec. 20, 2022.
Johnson, 2022, "How to Best Treat Acne Scars," Medical News Today (online website: [(https://www.medicalnewstoday.com/articles/324784, pp. 1-14)].
Antiperspirants-and-Deodorants: Principles of Underarm Technology, Micelle press IFSCC No. 6.

(Continued)

*Primary Examiner* — Hong Yu

(57) ABSTRACT

Described herein are personal care compositions, which provide—inter alia—sweat reduction. The personal care compositions described herein may comprise humectants, thickeners, alpha hydroxy acids, and a carrier; and are typically free of added aluminum-based antiperspirant actives.

20 Claims, No Drawings

(56) References Cited

U.S. PATENT DOCUMENTS

| | | |
|---|---|---|
| 2020/0405674 A1 | 12/2020 | Schiller et al. |
| 2021/0275418 A1 | 9/2021 | Bhardwaj et al. |
| 2021/0275419 A1 | 9/2021 | Li |
| 2021/0283025 A1 | 9/2021 | Das et al. |
| 2021/0299020 A1 | 9/2021 | Cruz et al. |
| 2022/0031591 A1 | 2/2022 | Botto et al. |
| 2022/0079854 A1 | 3/2022 | Li et al. |
| 2022/0241162 A1 | 8/2022 | Fan et al. |
| 2022/0395437 A1 | 12/2022 | Leva |

FOREIGN PATENT DOCUMENTS

| | | |
|---|---|---|
| CN | 101820753 | 9/2010 |
| CN | 103690380 | 4/2014 |
| CN | 109259188 | 1/2019 |
| DE | 19643585 | 4/1998 |
| DE | 102004032734 | 10/2005 |
| EP | 0345082 | 12/1989 |
| EP | 0749749 | 12/1996 |
| EP | 1443892 | 8/2004 |
| EP | 1510200 | 3/2005 |
| EP | 1526827 | 5/2005 |
| EP | 2353579 | 8/2011 |
| EP | 2374835 | 10/2011 |
| JP | H09110650 | 4/1997 |
| JP | 2004-089177 | 3/2004 |
| KR | 20120070104 | 6/2012 |
| KR | 101189187 | 10/2012 |
| KR | 20140039548 | 4/2014 |
| KR | 20150011060 | 1/2015 |
| KR | 101503979 | 3/2015 |
| KR | 101768921 | 8/2017 |
| WO | 2009/020582 | 2/2009 |
| WO | 2009/046008 | 4/2009 |
| WO | 2010/044076 | 4/2010 |
| WO | 2011/099849 | 8/2011 |
| WO | 2017/030560 | 2/2017 |
| WO | 2018/022016 | 2/2018 |
| WO | 2019/117858 | 6/2019 |
| WO | 2020/052916 | 3/2020 |
| WO | 2020/057761 | 3/2020 |
| WO | 2020/185654 | 9/2020 |
| WO | 2021/096518 | 5/2021 |
| WO | 2021/183462 | 9/2021 |
| WO | 2021/183464 | 9/2021 |
| WO | 2022/063857 | 3/2022 |
| WO | 2023/034493 | 3/2023 |

OTHER PUBLICATIONS

Boyd (https://www.chemservice.com/news/2014/08/which-chemicals-make-deodorants-and-antiperspirants-work/), Aug. 22, 2014, pp. 1-2 (Year:2014).
Evans et al., 2012, "Axillary skin biology and care", International Journal of Cosmetic Science, 34:389-395.
International Search Report and the Written Opinion of the International Searching Authority issued in International Application PCT/US2019/061522 mailed May 12, 2020.
Allies Group, 2017, "Promise Keeper Blemish Facial", Mintel Database GNPD AN: 5196555.
Anonymous, "Ingredients of Filorga Ultimate Revitalizing Night Cream," retrieved from https://www.cosdna.com/chs/cosmetic_4251189624.html, published on May 16, 2015.
Briseis, 2005, "Intensity Classic Deo Roll-On", Mintel Database GNPD AN: 371579.
Coop, 2014, "Intimate Wash", Mintel Database GNPD AN: 2677521.
Dr. Dennis Gross Skincare, 2014, "Clinical Concentrate Radiance Booster", Mintel Database GNPD AN: 2350479.
Glamglow, 2012, "Super-Mud Clearing Treatment", Mintel Database GNPD AN: 1921209.
Glamglow, 2019, "Superserum 6-Acid Refining Treatment", Mintel Database GNPD AN: 6521601.
Glamglow, 2019, "Supertoner Exfoliating Acid Soution", Mintel Database GNPD AN: 6457009.
International Search Report and the Written Opinion of the International Searching Authority issued in International Application PCT/US2020/021657 mailed May 27, 2020.
International Search Report and the Written Opinion of the International Searching Authority issued in International Application PCT/US2021/021426 mailed Jun. 28, 2021.
International Search Report and the Written Opinion of the International Searching Authority issued in International Application PCT/US2021/021428 mailed Jun. 28, 2021.
International Search Report and the Written Opinion of the International Searching Authority issued in International Application PCT/US2022/042563 mailed Jan. 20, 2023.
Jphnson & Johnson, 2006, "Micro Exfoliating Oxygenating Gel", Mintel Database GNPD AN: 598917.
Laboratoire SVR, 2017, "48H Anti-Perspirant Deodorant Roll-on", Mintel Database GNPD AN: 5111953.
Novartis Consumer Health, 2011, "Milk Body Lotion", Mintel Database GNPD AN: 1632704.
Personal Collection, 2018, "Shaveless Hair Minimizing Anti-Perspirant Deodorant Roll-On", Mintel Database GNPD AN: 5574907.
Skin Design London, 2017, "Acne On The Spot Serum", Mintel Database GNPD AN: 4688909.
WPI Thomson Database AN: 2019-11530B and CN 109259188.
Celltrion Skincure, 2021, "Cleansing Oil & Blackhead", Mintel Database GNPD AN: 8549187.
Coreana Cosmetics, 2020, "Peeling Pad", Mintel Database GNPD AN: 7440987.
International Search Report and the Written Opinion of the International Searching Authority issued in International Application PCT/US2023/084725 mailed Mar. 28, 2024.
Cork, 1996, "The role of *Staphylococcus aureus* in atopic eczema: treatment strategies", Journal of the European Academy of Dermatology and Venereology, vol. 7, Suppl. 1, pp. 31-37.
Cosinter, 2011, "Intimate Liquid Soap", Mintel Database GNPD AN: 1547745.
Do Couto et al., 2016, "Antifungal Activity of the Piroctone Olamine in Intra-Abdominal Candidiasis", Spinger Plus, 5:468.
International Search Report and the Written Opinion of the International Searching Authority issued in International Application PCT/US2023/031519 mailed Nov. 30, 2023.
International Search Report and the Written Opinion of the International Searching Authority issued in International Application PCT/US2023/031632 mailed Nov. 30, 2023.
Patel, 2014, "Postinflammatory hyperpigmentation: Review of pathogenesis, prevention, and treatment", Pigment International, vol. 1, Issue 2, pp. 59-69.
Pharma Solutions, 2022, "Cleansing Bar", Mintel Database GNPD AN: 9713532.

\* cited by examiner

PERSONAL CARE COMPOSITIONS

CROSS-REFERENCE TO RELATED APPLICATION

This application claims the benefit of priority from U.S. Provisional Application No. 63/260875, entitled "ANTI-PERSPIRANT COMPOSITIONS FREE-FROM ALUMINUM SALTS" and filed Sep. 3, 2021, the contents of which are hereby incorporated herein in their entirety.

FIELD OF THE DISCLOSURE

Personal care compositions, specifically antiperspirant/deodorant compositions, are often used to reduce the perspiration in an axillary region and to treat or prevent the growth of bacteria in this region, thereby to reduce or eliminate body odor. Aluminum salts, specifically aluminum chlorohydrate, have been widely used as antiperspirant actives to block sweat pores, preventing the growth in armpit microorganisms. However, there is a growing desire to replace these salts with other active ingredients.

BACKGROUND

There is a wide array of bacteria that reside on our skin, especially in the axillary region. The most common bacterial genus on our skin is Staphylococcus bacteria, which includes *Staphylococcus epidermidis*, one of the most studied and known microbes. While *Staphylococcus epidermidis* has demonstrated some benefits to skin, other bacteria, such as Corynebacteria have proven to be undesirable. There is ample evidence to indicate that Corynebacteria (Coryneforms) are the primary source of undesired, pungent underarm odors. By reducing the underarm seat, the growth of detrimental bacteria will be reduced or eliminated, therefore the malodor is controlled.

BRIEF SUMMARY

The present invention relates to personal care compositions, specifically antiperspirant/deodorant compositions, which provide sweat reduction. The present invention relates to personal care compositions, specifically antiperspirant/deodorant compositions, which are free-from aluminum salts and provide sweat reduction. The antiperspirant/deodorant compositions of the invention comprise humectants, thickeners, preservatives, alpha hydroxy acids, carriers, fragrances, and are free-from aluminum salts.

The antiperspirant/deodorant compositions described in the present disclosure are free of added metallic salts used as antiperspirant actives. The antiperspirant/deodorant compositions described in the present disclosure are free of zinc-based antiperspirant actives, of iron-based antiperspirant actives, of zirconium-based antiperspirant actives and of magnesium-based antiperspirant actives. In one embodiment, the present invention provides a method of reducing sweat in the axillary region, using the antiperspirant/deodorant compositions according to the present invention.

In another embodiment, the present invention provides a method of reducing malodor in the axillary region caused by excessive sweat, using the antiperspirant/deodorant compositions according to the present invention.

The antiperspirant/deodorant compositions of the invention can be formulated into topical formulations suitable for application to skin, illustrative examples being: a stick, a gel, a glide, a cream, a roll-on, a soft solid, wipes, a powder, a liquid, an emulsion, a suspension, dispersion, an aerosol, or a spray. The antiperspirant/deodorant compositions of the invention can comprise a single phase or can be a multi-phase system; for example, a system comprising a polar phase and oil phase, optionally in the form of a stable emulsion. The antiperspirant/deodorant compositions can be liquid, semi-solid, or solid. The antiperspirant and/or deodorant compositions can be provided in any suitable container such as an aerosol can, tube, or container with a porous cap, roll-on container, bottle, container with an open end, or the like.

The antiperspirant/deodorant compositions can be used in a method to reduce sweating by applying the antiperspirant/deodorant compositions to skin. In certain embodiments, the application is to axilla.

In one embodiment, the invention provides antiperspirant/deodorant compositions comprising inhibiting and/or reducing the growth of detrimental bacteria, responsible for the malodor. By reducing the sweat, the antiperspirant/deodorant compositions reduce the formation of the detrimental bacteria responsible for the malodor.

In another embodiment, the invention provides an antiperspirant/deodorant composition comprising humectants, thickeners, preservatives, alpha hydroxy acids, carriers and fragrances.

In other embodiments, the invention provides an antiperspirant/deodorant composition, wherein the antiperspirant/deodorant composition is free-from aluminum salts.

In yet other embodiment, the invention provides an antiperspirant/deodorant composition, wherein the antiperspirant/deodorant composition is formulated as a stick, a gel, a glide, a cream, a roll-on, a soft solid, wipes, pads, towelette, soft solid, a powder, a liquid, an emulsion, a suspension, a dispersion, an aerosol, or a spray. In yet another embodiment, the invention provides an antiperspirant/deodorant composition, wherein the antiperspirant/deodorant composition is formulated as a roll-on.

In one embodiment, the invention provides an antiperspirant/deodorant composition, wherein the humectants are selected from among vegetable refined glycerin, non-crystal sorbitol, xylitol, propylene glycol, polyethylene glycol, polyoxyethylenes, ethylene glycol, diethylene glycol, hexylene glycol, butylene glycol and combinations thereof.

In some embodiments, the invention provides an antiperspirant/deodorant composition, wherein the humectant comprises vegetable refined glycerin. In some embodiments, the invention provides an antiperspirant/deodorant composition, wherein the humectant comprises polyethylene glycol. In some embodiments, the invention provides an antiperspirant/deodorant composition, wherein the humectant comprises polyethylene glycol and vegetable refined glycerin.

In another embodiment, the invention provides an antiperspirant/deodorant composition, wherein the humectant is comprised from about 5 to about 30% by weight, or from about 10 to about 20% by weight, of the total weight of the antiperspirant/deodorant composition.

In yet another embodiment, the invention provides an antiperspirant/deodorant composition, wherein the thickeners are selected from among hydroxypropyl methylcellulose, polyethylene glycols, polyacrylic acids, cross-linked homopolymer of acrylic acid, acrylates of $C_{10-30}$ alkyl acrylate crosspolymer and combinations thereof.

In some embodiments, the invention provides an antiperspirant/deodorant composition, wherein the thickener comprises hydroxypropyl methylcellulose. In some embodiments, the invention provides an antiperspirant/deodorant composition, wherein the thickener comprises polyethylene glycol. In some embodiments, the invention provides an antiperspirant/deodorant composition, wherein the thickener comprises hydroxypropyl methylcellulose and polyethylene glycol.

In one embodiment, the invention provides an antiperspirant/deodorant composition, wherein the thickeners are comprised from about 1 to about 5% by weight of the antiperspirant/deodorant composition.

In one embodiment, the invention provides an antiperspirant/deodorant composition, wherein the preservatives are selected from among caprylyl glycol, phenoxyethanol, butylated hydroxytoluene, ethylenediaminetetraacetic acid, ethylhexylglycerin, citric acid, benzoic acid, and combinations thereof.

In some embodiments, the invention provides an antiperspirant/deodorant composition, wherein the preservatives are comprised from about 0.1 to about 10% by weight of the antiperspirant/deodorant composition. In some embodiments, the invention provides an antiperspirant/deodorant composition, wherein the preservative comprises caprylyl glycol.

In other embodiments, the invention provides an antiperspirant/deodorant composition, wherein the alpha hydroxy acids are selected from among mandelic acid, glycolic acid, citric acid, lactic acid, malic acid, tartaric acid, phytic acid, hydroxycaprylic acid, hydroxycapric acid and combinations thereof.

In some embodiments, the invention provides an antiperspirant/deodorant composition, wherein the alpha hydroxy acids are comprised from about 0.05 to about 2% by weight of the antiperspirant/deodorant composition. In some embodiments, the invention provides an antiperspirant/deodorant composition, wherein the alpha hydroxy acid is lactic acid.

In one embodiment, the invention provides an antiperspirant/deodorant composition, further comprising plant based oils, fragrances, surfactants, antioxidants, antibacterial agents, deodorizing agents, skin soothing agents, vitamins, pH adjusters, polymers, or combinations thereof.

In another embodiment, the invention provides an antiperspirant/deodorant composition, comprising about 5 to about 30% by weight humectants, about 1 to about 5% by weight thickeners, about 0.1 to about 10% by weight preservatives, and about 0.05 to about 2% by weight alpha hydroxy acids.

In one embodiment, the invention provides a method of reducing sweat of a subject in need thereof, comprising applying the antiperspirant/deodorant composition of the invention, to the axillary region of the subject in need thereof.

In other embodiments, the invention provides a method of reducing sweat from about 10 to about 40%, or from about 15 to about 20%, or from about 25 to about 30%, or from about 30 to about 35%, or from about 35 to about 40%.

In some embodiments, the invention provides a method of reducing sweat of a subject in need thereof, wherein the sweat reduction is of at least 20%. In some embodiments, the invention provides a method of reducing sweat of a subject in need thereof, wherein the sweat reduction is of at least 30%.

In one embodiment, the invention provides a method of reducing malodor in the axillary region caused by excessive sweat, comprising applying the antiperspirant/deodorant composition of the invention, to the axillary region of a subject in need thereof.

DETAILED DESCRIPTION

It is to be understood that both the foregoing general description and the following detailed description of the invention, are exemplary and explanatory only and are not restrictive of the claimed invention.

As used herein, the use of the singular includes the plural unless specifically stated otherwise. For example, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Any value within the range can be selected as the terminus of the range. Thus, a range from 1-5, includes specifically 1, 2, 3, 4 and 5, as well as subranges such as 2-5, 3-5, 2-3, 2-4, 1-4, etc.

The term "about" when referring to a number means any number within a range of 10% of the number. For example, the phrase "about 2.0 wt. %" refers to a number between and including 1.8 wt. % and 2.2 wt. %.

As used herein, the use of a compound comprising several isomers or stereoisomers includes all the isomeric forms of that compound. When referring to chemical structures, and names, the symbols "C", "H", and "O" mean carbon, hydrogen, and oxygen, respectively. The symbols "—", "=" and "≡" mean single bond, double bond, and triple bond respectively. For readability purposes, the chemical functional groups are in their adjective form; for each of the adjective, the word "group" is assumed. For example, the adjective "alkyl" without a nouns thereafter, should be read as "an alkyl group."

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the personal care compositions of the instant disclosure can be free or essentially free of all components and elements positively recited throughout the instant disclosure. In some instances, the personal care compositions of the present disclosure may be substantially free of non-incidental amounts of the ingredient(s) or compound(s) described herein. A non-incidental amount of an ingredient or compound is the amount of that ingredient or compound that is added into the personal care composition by itself. For example, a personal care composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the personal care composition includes both components (or the composition includes more than two components that overlap), an overlapping compound does not represent more than one component. For example, caprylyl glycol may be characterized as both a humectant and a preservative. If a particular personal care composition includes both a humectant and a preservative, caprylyl glycol will serve only as either a humectant or a preservative—not both.

Unless stated otherwise, all percentages of the personal care composition components given in this specification are by weight based on a total oral care composition or formulation weight of 100%. Weight percentages may be referred to herein as "wt. %".

As used herein, the terms "composition" and "formulation" can be used interchangeably within the specification. As used herein, the term "antiperspirant" refers to a product applied topically that reduces the production of perspiration (sweat) at that site. As used herein the term "reduce" in the "reduce sweat" context, refers to decrease or lessen of the dampness, perspiration, or wetness in the applied area. As used herein, the term "deodorant" refers to inhibiting the odor causing bacteria that makes the sweat smell. As used herein, the term "antiperspirant/deodorant compositions" refers to compositions which provide an antiperspirant effect and/or a deodorant effect.

As used herein, the term "free of aluminum-based antiperspirant actives", means that the antiperspirant/deodorant compositions of the present disclosure do not comprise one or more of aluminum-based antiperspirant actives. Aluminum-based antiperspirant actives are not added to the antiperspirant/deodorant compositions of the invention to display some antiperspirant/deodorant effect.

As used herein, the term "aluminum free" or "free-from aluminum" means that the antiperspirant/deodorant composition does not contain any aluminum-based antiperspirant. Non limiting examples of aluminum-based antiperspirant actives, can include those listed in the US antiperspirant monograph, such as, aluminum chlorohydrate, aluminum chloride, aluminum dichlorohydrate, aluminum sesquichlorohydrate poylethylene glycol, aluminum sesquichlorohydrate propylene glycol, aluminum zirconium octachlorohydrate, aluminum zirconium pentachlorohydrate, aluminum zirconium tetrachlorohydrate, aluminum zirconium trichlorohydrate, aluminum sesquichlorohydrate, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex propylene glycol (aluminum chlorohydrex PG), aluminum chlorohydrex polyethylene glycol (aluminum chlorohydrex PEG), aluminum dichlorohydrex propylene glycol (aluminum dichlorohydrex PG), and aluminum dichlorohydrex polyethylene glycol (aluminum dichlorohydrex PEG).

As used herein, the term "zirconium free" or "free-from zirconium-based antiperspirant actives" means that the antiperspirant/deodorant composition does not contain any zirconium-based antiperspirant. Non limiting examples of zirconium-based antiperspirant actives, include aluminum zirconium octachlorohydrate, aluminum zirconium pentachlorohydrate, aluminum zirconium tetrachlorohydrate, aluminum zirconium trichlorohydrate, and aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly).

As used herein, the term "free of zinc-based antiperspirant actives", means that the antiperspirant/deodorant composition does not comprise one or more of zinc-based antiperspirant actives. Zinc-based antiperspirant actives are not added to the antiperspirant/deodorant compositions of the invention to display some antiperspirant/deodorant effect. Non limiting examples of zinc-based antiperspirant actives can include one or more of zinc oxide, zinc hydroxide, zinc hydroxide ions with counter ions, and zinc ions with counter ions.

As used herein, the term "free of iron-based antiperspirant actives", means that the antiperspirant/deodorant composition does not comprise one or more of iron-based antiperspirant active.

As used herein, the term "free of titanium-based antiperspirant actives", means that the antiperspirant/deodorant composition does not comprise one or more of titanium-based antiperspirant active. For example, the antiperspirant/deodorant compositions may include a reduced amount, be substantially free of, or free of titanium-based antiperspirant actives, such as ammonium titanium lactate and the like.

As used herein, the term "free of magnesium-based antiperspirant actives", means that the antiperspirant/deodorant composition does not comprise one or more of magnesium-based antiperspirant actives. Non-limiting examples of magnesium-based actives include, but are not limited to, magnesium chloride, magnesium bromide, magnesium fluoride and organic salts such as various alkyl chain length substituted carboxylic acids, magnesium oxide, and magnesium hydroxide. As used herein, the term "axilla" or "axillary region" refers to the armpit or underarm of the body.

The antiperspirant/deodorant compositions may be substantially free or free of aluminum-based antiperspirant, magnesium-based antiperspirant actives, titanium-based antiperspirant actives, free-from zirconium-based antiperspirant actives, and zinc-based antiperspirant actives. For example, the antiperspirant/deodorant compositions may have about 3 wt. % or less, about 2 wt. % or less, about 1 wt. % or less, about 0.5 wt. % or less, about 0.1 wt. % or less, about 0.05 wt. % or less, or about 0.01 wt. % or less of aluminum-based antiperspirant, magnesium-based antiperspirant actives, titanium-based antiperspirant actives, free-from zirconium-based antiperspirant actives, and zinc-based antiperspirant actives (individually or cumulatively), based on the total weight of the antiperspirant/deodorant composition. In some embodiments, the antiperspirant/deodorant compositions have about 0 wt. % or 0 wt. % of aluminum-based antiperspirant, magnesium-based antiperspirant actives, titanium-based antiperspirant actives, free-from zirconium-based antiperspirant actives, and zinc-based antiperspirant actives (individually or cumulatively), based on the total weight of the antiperspirant/deodorant composition.

Aspects of the invention are directed to antiperspirant/deodorant compositions that provide a reduction of sweat while being free-from aluminum-based antiperspirant and, preferably, free of magnesium-based antiperspirant actives, titanium-based antiperspirant actives, free-from zirconium-based antiperspirant actives, and zinc-based antiperspirant actives. The inventors discovered that certain embodiments of antiperspirant/deodorant compositions containing specific combinations of ingredients in particular amounts and ratios provides a reduction of sweat of about 20% or more while being free from free-from aluminum-based antiperspirant, magnesium-based antiperspirant actives, and zinc-based antiperspirant actives.

The antiperspirant/deodorant compositions as disclosed herein, may retard the sweating process by reducing the amount of perspiration excreted from the eccrine sweat glands and/or apocrine sweat glands. In certain embodiments, the antiperspirant/deodorant composition provides a reduction of sweat of about 20% or more, about 23% or more, about 26% or more, about 29% or more, about 32% or more, about 35% or more, about 36% or more, about 40% or more, about 44% or more, or about 48% or more, preferably, over a 24-hour period after application. For example, the antiperspirant/deodorant composition may provide a reduction of swear (e.g., produce a reduction of sweat when applied to skin) of about 20 to about 48%, about 20 to about 45%, about 20 to about 40%, about 20 to about 36%, about 20 to about 32%, about 20 to about 28%; from about 24 to about 48%, about 24 to about 45%, about 24 to about 40%, about 24 to about 36%, about 24 to about 32%, about 24 to about 28%; from about 28 to about 48%, about 28 to about 45%, about 28 to about 40%, about 28 to about 36%, about 28 to about 32%; from about 32 to about 48%, about 32 to about 45%, about 32 to about 40%, about 32 to about 36%; from about 36 to about 48%, about 36 to about 45%, about 36 to about 40%, or any range or subrange thereof, preferably, over a 24-hour period after application. The antiperspirant/deodorant composition provides a reduction of sweat according to any of the foregoing listed ranges and/or percentages over a 36-hour period.

In some embodiments, the invention provides antiperspirant/deodorant compositions that inhibit and/or reduce the growth of detrimental bacteria, responsible for the underarm malodor. By reducing the underarm sweat, the antiperspirant and/or deodorant compositions will reduce the formation of the detrimental bacteria responsible for the malodor. According to at least one aspect, a method is provided for reducing sweat in the axillary region, e.g., by applying the antiperspirant/deodorant compositions to the axillary region. In accordance with another aspect, provided is a method of reducing malodor caused by excessive sweat using the antiperspirant/deodorant compositions according to the present invention.

The antiperspirant/deodorant compositions can be used in a method to reduce sweat by applying the antiperspirant/deodorant compositions to the skin. In certain embodiments, the application is to axilla. In other embodiments, the invention provides a method of reducing sweat from about 10 to about 40%, or from about 15 to about 20%, or from about 25 to about 30%, or from about 30 to about 35%, or from about 35 to about 40%.

In some embodiments, the invention provides a method of reducing sweat of a subject in need thereof, wherein the sweat reduction is of at least 20%. In some embodiments, the invention provides a method of reducing sweat of a subject in need thereof, wherein the sweat reduction is of at least 30%.

The antiperspirant/deodorant compositions of the invention can be formulated into topical antiperspirant and/or deodorant formulations suitable for application to the skin. The antiperspirant/deodorant composition o the invention can be a stick, a glide, a gel, a cream, a roll-on, a soft solid, wipes, pads, towelette, soft solid, a powder, a liquid, an emulsion, a suspension, a dispersion, an aerosol, or a spray. The antiperspirant/deodorant composition of the invention can be a single phase or can be a multi-phase system. The antiperspirant/deodorant compositions of the invention can have a polar phase and an oil phase in the form of a stable emulsion. The antiperspirant/deodorant compositions can be liquid, semi-solid or solid. The antiperspirant/deodorant compositions can be provided in any suitable container such as an aerosol can, tube, container with a porous cap, roll-on container, bottle, container with an open end, cardboard container, box, or the like. In some embodiments, the antiperspirant/deodorant compositions can be contained in any roll-on dispenser that has a ball or the like or a domed surface, for applying the antiperspirant/deodorant compositions to the surface of the skin.

Suitable components, such as those listed below, may be included or excluded from the formulations for the antiperspirant/deodorant compositions care compositions depending on the specific combination of other components, the form of the hair care compositions, and/or the use of the formulation (e.g., a roll-on, stick, spray, etc.).

The antiperspirant/deodorant compositions as disclosed herein, typically comprise one or more humectant(s), one or more alpha hydroxyl acid(s), an one or more carrier(s), wherein the antiperspirant/deodorant compositions is free-from aluminum salts. The antiperspirant/deodorant compositions typically comprise hygroscopic agents or humectant agents. Humectants help bind water in the skin and keep it there for a longer period of time. Humectants attract and trap water. In some embodiments, the hygroscopic agents or humectant agents are selected from among glycerin (such as, vegetable refined glycerin), polyhydric alcohols, low molecular weight polyethylene glycols (PEGs) and polyoxyethylenes. Examples of polyhydric alcohols include, but are not limited to, sorbitol (e.g., non-crystal sorbitol), xylitol, propylene glycol, dipropylene glycol, polypropylene glycols (having three or more propylene monomer units), ethylene glycol, diethylene glycol, hexylene glycol, butylene glycol, and combinations thereof. In some embodiments, the hygroscopic agents or humectant agents are glycerin (e.g., vegetable glycerin), propylene glycol or polyethylene glycol, 1,2-pentylene glycol and/or a combination thereof.

High molecular weight PEGs are also suitable as humectants, including those having an average molecular weight of about 200,000 [Da] to about 7,000,000 [Da], for example about 500,000 [Da] to about 5,000,000 [Da] or about 1,000,000 [Da] to about 2,500,000 [Da].

The humectants may be chosen from glycerin, butylene glycol, and 1,3-propanediol, polyglutamic acid, saccharide isomerate, and combinations thereof. In some embodiments, the hygroscopic agent or the humectant agent is vegetable refined glycerin. In some embodiments, the hygroscopic agent or the humectant agent is polyethylene glycol 600 (CAS-25322-68-3). In some embodiments, the hygroscopic agent or the humectant agent is a combination of polyethylene glycol 600 and vegetable glycerin. In personal care compositions, glycerin helps the skin to attract and retain its own natural moisture, leaving it feeling soft. Rather than sitting on top of the skin, glycerin softens the skin while permitting it to breathe. Glycerin and glycerol are both names for the same molecule. On a molecular level, glycerin is small enough to penetrate deeper into the skin and be easily absorbed. By reducing the sweat, the antiperspirant/deodorant compositions reduce the formation of the detrimental bacteria responsible for the malodor.

In some embodiments, the antiperspirant/deodorant compositions comprise hygroscopic agents or humectants from about 5 to about 30% by weight of the total weight of the antiperspirant/deodorant composition. For example, the amount of humectant or hygroscopic agent present in the antiperspirant/deodorant compositions may be from about 5 to about 30 wt. %, about 5 to about 25 wt. %, about 5 to about 22 wt. %, about 5 to about 20 wt. %, about 5 to about 18 wt. %, about 5 to about 16 wt. %; from about 8 to about 30 wt. %, about 8 to about 25 wt. %, about 8 to about 22 wt. %, about 8 to about 20 wt. %, about 8 to about 18 wt. %, about 8 to about 16 wt. %; from about 10 to about 30 wt. %, about 10 to about 25 wt. %, about 10 to about 22 wt. %, about 10 to about 20 wt. %, about 10 to about 18 wt. %, about 10 to about 16 wt. %; from about 12 to about 30 wt. %, about 12 to about 25 wt. %, about 12 to about 22 wt. %, about 12 to about 20 wt. %, about 12 to about 18 wt. %, about 12 to about 16 wt. %; from about 14 to about 30 wt. %, about 14 to about 25 wt. %, about 14 to about 22 wt. %, about 14 to about 20 wt. %, about 14 to about 18 wt. %, about 14 to about 16 wt. %, including ranges and subranges thereof, based on the total weight of the antiperspirant/deodorant composition. In some embodiments the antiperspirant/deodorant compositions of the invention comprise hygroscopic agents or humectants in about 10 to about 20% by weight of the total weight of the antiperspirant/deodorant composition. In some embodiments, the antiperspirant/deodorant compositions of the invention comprise hygroscopic agents or humectants in about 15 to about 18% by weight of the total weight of the antiperspirant/deodorant composition. In some embodiments, the antiperspirant/deodorant compositions of the invention comprise hygroscopic agents or humectants in about 15% by weight of the total weight of the antiperspirant/deodorant composition. In some embodiments, the antiperspirant/deodorant compositions of the invention comprise hygroscopic agents or humectants in about 10% by weight of the total weight of the antiperspirant/deodorant composition.

In some embodiments, the antiperspirant/deodorant compositions of the invention comprise thickeners. The thickeners may be chosen from polysaccharides; carboxylic acid polymers; crosslinked polyacrylate polymers; polyacrylamide polymers; gums, and combinations of two or more thereof. Examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

Non-limiting examples of carboxylic acid polymers include crosslinked carboxylic acid polymers containing one or more monomers derived from acrylic acid, substituted acrylic acids, and salts and esters of these acrylic acids and the substituted acrylic acids, such as carbomers. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

In certain cases, the aqueous liquid composition may be formulated to have thickening polymers, such as polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and/or starch derivatives (for example, starch oxide, dialdehyde starch, dextrin, British gum, acetyl starch, starch phosphate, carboxymethyl starch, hydroxyethyl starch, hydroxypropyl starch). In some embodiments, the thickeners are selected from among hydroxypropyl methylcellulose, polyethylene glycols (PEGs), polyacrylic acids (sold under the name of Carbopol), cross-linked homopolymer of acrylic acid (sold under the name of Carbopol® Ultrez 30 polymer), and acrylates of $C_{10-30}$ alkyl acrylate crosspolymer (sold under the name of Carbopol® Ultrez 20 polymer).

In some embodiments, the antiperspirant/deodorant compositions of the invention comprise two or more thickeners, such as those selected from hydroxypropyl methylcellulose and cross-linked homopolymer of acrylic acid (sold under the name of Carbopol® Ultrez 30 polymer). In some embodiments, the antiperspirant/deodorant compositions includes two, three, four, or five thickeners, or any range or subrange thereof. The thickener may be selected from hydroxypropyl methylcellulose, polyethylene glycols and combinations thereof. Acrylate copolymers sold under the name of EPITEX™ 66 is a combination of tert-butyl acrylate-ethyl acrylate-methacrylic acid polymer (159666-35-0), 2-propenoic acid, 2-methyl-, ethyl ester, polymer with methyl 2-methyl-2-propenoate (25685-29-4), 2-propenoic acid, 2-methyl-, polymer with butyl 2-propenoate and methyl 2-methyl-2-propenoate (25035-69) and 2-propenoic acid, 2-methyl-, polymer with ethyl 2-propenoate (25212-88-8). In some embodiments, the antiperspirant/deodorant compositions of the invention comprise EPITEX™ 66 in 1 to 3 wt. % relative to the total weight of the composition.

The antiperspirant/deodorant compositions of the invention comprise thickeners from about 1 to about 10 wt. % of the total weight of the antiperspirant/deodorant composition. For example, the antiperspirant/deodorant composition may include one or more thickener(s) in an amount from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about to about 4 wt. %, about 1 to about 2 wt. %; from about 2 to about 10 wt. %, about 2 to about 8 wt. %, about 2 to about 6 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to 10 wt. %, or any range or subrange thereof, based on the total weight of the antiperspirant/deodorant composition. In some instances, the antiperspirant/deodorant compositions of the invention comprise thickeners from about 1 to about 3 wt. %, or from about 3 to about 5 wt. % based on the total weight of the antiperspirant/deodorant composition. The antiperspirant/deodorant compositions of the invention comprise thickeners in about 1.35 wt. %, based on the total weight of the antiperspirant/deodorant composition. The antiperspirant/deodorant compositions of the invention comprise thickeners in about 3.75 wt. %, based on the total weight of the antiperspirant/deodorant composition.

In some embodiments, the antiperspirant/deodorant compositions of the invention comprise anti-foaming agents or preservatives. The antiperspirant/deodorant compositions may comprise preservatives selected from among caprylyl glycol, phenoxyethanol, butylated hydroxytoluene (BHT), ethylenediaminetetraacetic acid (EDTA), ethylhexylglycerin, citric acid, benzoic acid, and combinations thereof. In some embodiments the anti-foaming agent or preservative is caprylyl glycol. Caprylyl glycol is also known as 1,2-octanediol.

The antiperspirant/deodorant compositions of the invention comprise anti-foaming agents or preservatives from about 0.1 to about 10 wt. %, based on the total weight of the antiperspirant/deodorant composition. For instance, the antiperspirant/deodorant composition may include one or more thickener(s) in an amount from about 0.1 to about 10 wt. %, about 0.1 to about 8 wt. %, about 0.1 to about 6 wt. %, about 0.1 to about 4 wt. %, about 0.1 to about 2 wt. %, about 0.1 to about 1 wt. %; from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about to about 4 wt. %, about 1 to about 2 wt. %; from about 2 to about 10 wt. %, about 2 to about 8 wt. %, about 2 to about 6 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to 10 wt. %, or any range or subrange thereof, based on the total weight of the antiperspirant/deodorant composition. The antiperspirant/deodorant compositions of the invention comprise anti-foaming agents or preservatives from about 0.1 to about 2 wt. %, based on the total weight of the antiperspirant/deodorant composition. The antiperspirant/deodorant compositions of the invention comprise anti-foaming agents or preservatives in about 0.3 wt. %, based on the total weight of the antiperspirant/deodorant composition.

In some embodiments, the antiperspirant/deodorant compositions of the invention comprise alpha hydroxy acids. For example, the personal care formulation may include one or more one or more alpha hydroxy acid(s), such as those selected from $C_3$ to $C_7$ alpha-hydroxy acid or $C_4$ to $C_6$ alpha-hydroxy acid. In some embodiments, the personal care formulation includes a salt of an alpha-hydroxy acid. The salt of the alpha-hydroxy acid is preferably a sodium salt or a potassium salt. In at least one embodiment, the salt is a sodium salt (i.e., the cation associated with the salt is a sodium). Non-limiting examples of alpha hydroxy acids include but are not limited to, mandelic acid, glycolic acid, citric acid, lactic acid, malic acid, tartaric acid, phytic acid, hydroxycaprylic acid, hydroxycapric acid, glutaric acid, gluconic acid, or a combination of two or more thereof. In some embodiments, the alpha hydroxy acids are selected from among mandelic acid, glycolic acid, citric acid, lactic acid, malic acid, tartaric acid, phytic acid, hydroxycaprylic acid, hydroxycapric acid and combinations thereof. In further embodiments, the alpha hydroxy acids are citric acid, mandelic acid, glycolic acid, lactic acid or a combination of two or more thereof. In certain instance, the alpha-hydroxy acid is selected from malic acid, tartaric acid, alpha-hydroxy glutaric acid, gluconic acid, a salt thereof, and a combination of two or more thereof. Yet in further instances, the alpha-hydroxy acid or salt thereof is selected from lactic acid, malic acid, and sodium-D-gluconate. In at least one embodiment, the alpha hydroxy acid is lactic acid. In some embodiments the alpha hydroxy acid is lactic acid. The antiperspirant/deodorant compositions of the invention comprise alpha hydroxy acids from about 0.05 to about 2 wt. %, based on the total weight of the antiperspirant/deodorant composition.

The amount of alpha hydroxyl acid in the antiperspirant/deodorant compositions may be from about 0.05 to about 2 wt. %, about 0.05 to about 1.8 wt. %, about 0.05 to about 1.6 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %; from about 0.6 to about 2 wt. %, about 0.6 to about 1.8 wt. %, about 0.6 to about 1.6 wt. %, about 0.6 to about 1.4 wt. %, about 0.6 to about 1.2 wt. %, about 0.6 to about 1 wt. %; from about 0.9 to about 2 wt. %, about 0.9 to about 1.8 wt. %, about 0.9 to about 1.6 wt. %, about 0.9 to about 1.4 wt. %; from about 1.2 to about 2 wt. %, about 1.2 to about 1.8 wt. %, about 1.2 to about 1.6 wt. %; from about 1.5 to about 2 wt. %, about 1.5 to about 1.8 wt. %, or any range or subrange thereof, based on the total weight of the antiperspirant/deodorant composition. The antiperspirant/deodorant compositions of the invention comprise alpha hydroxy acids from about 0.1 to about 0.15 wt. %, from about 0.15 to about 1 wt. %, or from about 1 to about 2 wt. %, based on the total weight of the antiperspirant/deodorant composition. The antiperspirant/deodorant compositions of the invention comprise alpha hydroxy acids in about 0.15 wt. %, based on the total weight of the antiperspirant/deodorant composition.

In some embodiments, the antiperspirant/deodorant compositions of the invention comprise carriers or transporters. In general, carriers include but are not limited to, water or alcohols (e.g., ethanol, isopropanol or mixtures thereof). In at least one embodiment, the carrier comprises water. The amount of carrier present in the personal care formulation may vary, e.g., from about 5 to about 90 wt. %, based on the total weight of the personal care formulation. In some cases, the personal care formulation includes one or more carrier(s) in an amount from about 5 to about 75 wt. %, about 5 to about 50 wt. %, about 5 to about 25 wt. %, about 5 to about 15 wt. %; from about 25 to about 90 wt. %, about 25 to about 75 wt. %, about 25 to about 50 wt. %, about 25 to about 40 wt. %; from about 40 to about 90 wt. %, about 40 to about 75 wt. %, about 40 to about 60 wt. %; from about 60 to about 90 wt. %, about 60 to about 80 wt. %, about 60 to about 70 wt. %; from about 75 to about 90 wt. %, about 75 to about 85 wt. %; from about 80 to about 90 wt. %, about 85 to about 90 wt. %, or any ranges and subranges thereof, based on the total weight of the antiperspirant/deodorant composition. The carrier or transporter of choice is demineralized water. The content in carrier or transporter is present in any suitable amount capable of producing a stable composition to make a 100 wt. %, based on the weight of the antiperspirant/deodorant composition after all of the materials, including any optional materials, are added to the composition in their desired weight percentages. In some embodiments, the content in carrier or transporter is about 20 wt. %, or about 30 wt. %, or about 40 wt. %, or about 50 wt. %, or about 60 wt. %, or about 70 wt. %, or about 80 wt. %, or about 85 wt. %, based on the total weight of the antiperspirant/deodorant composition.

In some embodiments, the antiperspirant/deodorant compositions of the invention can comprise alpha hydroxy acids, beta hydroxy acids, polyhydroxy acids or combinations thereof. In some embodiments, the antiperspirant/deodorant compositions of the invention can comprise beta hydroxy acids. Non-limiting examples of beta hydroxy acids include salicylic acid, propionic acid, beta-hydroybutyric acid, beta-hydroxy beata-methylbutyric acid, carnitine, and combinations of two or more thereof. The beta hydroxy acids may in some cases be selected from salicylic acid, esters of salicylic acid, sodium salicylate, beta hydroxybutanoic acid, tropic acid, trethocanic acid, beta hydroxyl acids obtained from white willow bark extract and/or wintergreen leaves, and combinations of two or more thereof. In some embodiments, the beta hydroxy acid(s) comprises salicylic acid, sodium salicylate, beta hydroxyl acids of willow bark extract or combinations thereof. In one embodiment, the beta hydroxy acid is salicylic acid.

The amount of beta hydroxy acid in the antiperspirant/deodorant compositions may be from about 0.05 to about 2 wt. %, about 0.05 to about 1.8 wt. %, about 0.05 to about 1.6 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %; from about 0.6 to about 2 wt. %, about 0.6 to about 1.8 wt. %, about 0.6 to about 1.6 wt. %, about 0.6 to about 1.4 wt. %, about 0.6 to about 1.2 wt. %, about 0.6 to about 1 wt. %; from about 0.9 to about 2 wt. %, about 0.9 to about 1.8 wt. %, about 0.9 to about 1.6 wt. %, about 0.9 to about 1.4 wt. %; from about 1.2 to about 2 wt. %, about 1.2 to about 1.8 wt. %, about 1.2 to about 1.6 wt. %; from about 1.5 to about 2 wt. %, about 1.5 to about 1.8 wt. %, or any range or subrange thereof, based on the total weight of the antiperspirant/deodorant composition.

In some embodiments, the antiperspirant/deodorant compositions of the invention can comprise polyhydroxy acids. The polyhydroxy acids may include, but are not limited to, gluconolactone, gluconic acid, galactose, lactobionic acid, or combinations thereof. In some embodiments, the polyhydroxy acids are gluconolactone, lactobionic acid or combinations thereof. For instance, the polyhydroxy acid may be glucanodeltalactone.

The amount of polyhydroxy acid in the antiperspirant/deodorant compositions may be from about 0.05 to about 2 wt. %, about 0.05 to about 1.8 wt. %, about 0.05 to about 1.6 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %; from about 0.6 to about 2 wt. %, about 0.6 to about 1.8 wt. %, about 0.6 to about 1.6 wt. %, about 0.6 to about 1.4 wt. %, about 0.6 to about 1.2 wt. %, about 0.6 to about 1 wt. %; from about 0.9 to about 2 wt. %, about 0.9 to about 1.8 wt. %, about 0.9 to about 1.6 wt. %, about 0.9 to about 1.4 wt. %; from about 1.2 to about 2 wt. %, about 1.2 to about 1.8 wt. %, about 1.2 to about 1.6 wt. %; from about 1.5 to about 2 wt. %, about 1.5 to about 1.8 wt. %, or any range or subrange thereof, based on the total weight of the antiperspirant/deodorant composition.

In some embodiments, the antiperspirant/deodorant compositions comprise optional ingredients such as fragrances, surfactants, plant based oils, antioxidants, antibacterial agents, deodorizing agents, skin soothing agents, vitamins, pH adjusters, polymers, or combinations thereof.

In some embodiments, the antiperspirant/deodorant compositions of the invention comprise surfactants. In some embodiments, the antiperspirant/deodorant compositions of the invention comprise surfactants selected from among nonionic surfactants, anionic surfactants, cationic surfactants and amphoteric/zwitterionic surfactants. Examples of anionic surfactants include, but are not limited to, ammonium lauryl sulfate, ammonium lauryl ether sulfate, sodium lauryl sulfate, sodium lauryl ether sulfate, or a combination of two more thereof. For example, the anionic surfactant may be selected from ammonium lauryl sulfate, ammonium lauryl ether sulfate, and a combination of two or more thereof.

The amount of anionic surfactants in the antiperspirant/deodorant composition may be about 0.5 to about 10 wt. %, based on the total weight of the personal care composition. In some instances, the antiperspirant/deodorant composition include anionic surfactants in an amount from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about to about 4 wt. %, about 1 to about 2 wt. %; from about 2 to about 10 wt. %, about 2 to about 8 wt. %, about 2 to about 6 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to 10 wt. %, or any range or subrange thereof, based on the total weight of the antiperspirant/deodorant composition.

The amphoteric surfactants in the antiperspirant/deodorant compositions may be selected from a betaine, an alkyl sultaine, an alkyl amphoacetate, an alkyl amphoprionate, a salt thereof, and a combination of two or more thereof. Preferably, the amphoteric surfactant comprises a betaine surfactant. Non-limiting examples of betaine surfactants include cocamidopropyl betaine, cocodimethylcarboxymethylbetaine, lauryldimethylcarboxymethylbetaine, lauryldimethylcarboxyethylbetaine, cetyldimethyl-carboxymethylbetaine, lauryl-bis-(2-hydroxyethyl)-carboxymethylbetaine, oleyl-dimethylgammacarboxypropylbetaine, and lauryl-bis-(2-hydroxypropyl)-carboxyethyl-betaine, or a combination of two or more thereof.

The amount of amphoteric surfactants in the antiperspirant/deodorant composition may be about 0.5 to about 10 wt. %, based on the total weight of the personal care composition. In some instances, the antiperspirant/deodorant composition include amphoteric surfactants in an amount from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about to about 4 wt. %, about 1 to about 2 wt. %; from about 2 to about 10 wt. %, about 2 to about 8 wt. %, about 2 to about 6 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to 10 wt. %, or any range or subrange thereof, based on the total weight of the antiperspirant/deodorant composition.

In some embodiments, the surfactants are nonionic surfactants. In some embodiments, the nonionic surfactants include, but are not limited to, secondary alcohol ethoxylates, polyoxyethylene stearyl ethers, polyoxyethylene ethers, a mixture of high molecular mass saturated fatty alcohols, mainly cetyl alcohol and stearyl alcohol. The antiperspirant/deodorant compositions may include a non-ionic surfactant blend including two or more fatty alcohol ethoxylates, each having a polyethylene oxide chain length of at least 2. Preferred fatty alcohol ethoxylates generally have a fatty alcohol chain length of $C_{12}$ to $C_{24}$, a degree of unsaturation of 0-2, and a polyethylene oxide chain length of 2 to 150 ethylene oxide units. For example, the fatty alcohol ethoxylates may have the general formula: $CH_3—(CH_2)_x—CH2—O—(CH_2—CH_2—O—)_yH—$, where X=10-20, Y=2-100. In some cases, the blend of fatty alcohol ethoxylates includes at least one fatty alcohol ethoxylate having a long polyethylene oxide chain length and at least one fatty alcohol ethoxylate having a short polyethylene oxide chain length. Suitable long chain length fatty alcohol ethoxylates have a polyethylene oxide chain length greater than 20, preferably 21 to 150, more preferably 21 to 100. For example, the fatty alcohol ethoxylate may be a polyoxyethylene stearyl ethers having a structuring according to the chemical formula: $CH_3—(CH_2)_{16}—CH_2—(O—CH_2—CH2)_n—OH$ with average n being 2 to 20 respectively. Polyoxyethylene stearyl ethers compounds may in some cases be prepared by reacting stearyl alcohol with ethylene oxide.

Preferred long chain fatty alcohol ethoxylates include Steareth-100 (100 indicates the polyethylene oxide chain length) and Steareth 21. Other long chain fatty alcohol ethoxylates may be used, e.g., Ceteth-100, Oleth-100 Myreth-100, and Beheneth-100. These surfactants have a preferred HLB range from 15 to 8. Suitable short chain length fatty alcohol ethoxylates have a polyethylene oxide chain length of less than or equal to 20, preferably 2 to 20. Suitable shorter chain length fatty alcohol ethoxylates include, for example, Steareth-2, Steareth-10, Ceteth-20, Steareth-20, Myreth-20, Oleth-20 and Beheneth-20. These surfactants have a preferred HLB range from 4 to 16.

The non-ionic surfactants of the antiperspirant/deodorant composition may be selected from polyoxyethylene ethers, such as polyoxyethylene stearyl ethers compounds. The polyoxyethylene ethers may comprise a mixture of high molecular mass saturated fatty alcohols, such as cetyl alcohol and stearyl alcohol, and ethylene oxide. The polyoxyethylene ethers may be selected from Ceteareth-2, Ceteareth-3, Ceteareth-4, Ceteareth-5, Ceteareth-6, Ceteareth-7, Ceteareth-8, Ceteareth-9, Ceteareth-10, Ceteareth-11, Ceteareth-12, and a combination of two or more thereof. Examples of polyoxyethylene stearyl ethers compounds include Steareth-2, Steareth-4, Steareth-6, Steareth-7, Steareth-21, Steareth-10, Steareth-11, Steareth-13, Steareth-15, Steareth-20, or combinations of two or more thereof. The secondary alcohol ethoxylates are sold under the trade names of Tergitol®. Tergitol® surfactant is a nonionic surfactant available from Dow™.

The amount of nonionic surfactants (e.g., polyoxyethylene ethers and/or polyoxyethylene stearyl ethers) in the antiperspirant/deodorant composition may be about 0.5 to about 10 wt. %, based on the total weight of the personal care composition. In some instances, the antiperspirant/deodorant composition include nonionic surfactants (e.g., polyoxyethylene ethers and/or polyoxyethylene stearyl ethers) in an amount from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about to about 4 wt. %, about 1 to about 2 wt. %; from about 2 to about 10 wt. %, about 2 to about 8 wt. %, about 2 to about 6 wt. %, about 2 to about 4 wt. %; from about 4 to about 10 wt. %, about 4 to about 8 wt. %, about 4 to about 6 wt. %; from about 6 to about 10 wt. %, about 6 to about 8 wt. %; from about 8 to 10 wt. %, or any range or subrange thereof, based on the total weight of the antiperspirant/deodorant composition. In some cases, the antiperspirant/deodorant compositions may comprise surfactants from about 0.1 to about 5 wt. %, based on the total weight of the antiperspirant/deodorant composition. The antiperspirant/deodorant compositions of the invention comprise surfactants from about 1 to about 3 wt. %, based on the total weight of the antiperspirant/deodorant composition. The antiperspirant/deodorant compositions of the invention comprise surfactants in about 2 wt. %, based on the total weight of the antiperspirant/deodorant composition.

The antiperspirant/deodorant compositions of the invention may comprise Tergitol® in about 2 to about 5 wt. % based the total weight of the antiperspirant/deodorant composition. The antiperspirant/deodorant compositions of the invention comprise Tergitol® in about 2 wt. %, based on the total weight of the antiperspirant/deodorant composition. The antiperspirant/deodorant compositions of the invention comprise Tergitol® in about 3 wt. %, based on the total weight of the antiperspirant/deodorant composition. In some embodiments, the antiperspirant/deodorant compositions of the invention comprises an acrylates copolymer, such as EPITEX™ 66, in about 2 wt. %, relative to the total weight of the composition. In some embodiments, the antiperspirant/deodorant compositions of the invention comprises an acrylate copolymer, e.g., EPITEX™ 66, in about 3 wt. %, relative to the total weight of the composition.

In some embodiments, the antiperspirant/deodorant compositions of the invention comprise antioxidants. The antiperspirant/deodorant compositions of the invention comprise antioxidants from about 1 to about 5 wt. %, based on the total weight of the antiperspirant/deodorant composition. For instance, the amount of antioxidant present in the antiperspirant/deodorant composition may be from about 1 to about 5 wt. % wt. %, about 1 to about 4 wt. %, about 1 to about 3 wt. %, about 1 to about 2 wt. %; from about 2 to about 5 wt. % wt. %, about 2 to about 4 wt. %, about 2 to about 3 wt. %; from about 3 to about 5 wt. % wt. %, about 3 to about 4 wt. %; from about 4 to about 5 wt. %, or any range or subrange thereof, based on the total weight of the antiperspirant/deodorant composition. In some embodiments, the antiperspirant/deodorant compositions of the invention comprise antioxidants selected from among witch hazel, butylated hydroxytoluene, pentaerythrityl tetra-di-t-butyl hydroxyhydrocinnamate or combinations thereof. Pentaerythrityl tetra-di-t-butyl hydroxyhydrocinnamate is commercially available under the name of Tinogard TT™ by Ciba/BASF. In some embodiments, the antiperspirant/deodorant compositions of the invention comprise witch hazel in about 2 wt. %, relative to the total weight of the composition.

Any known fragrance can be used in any desired amount. The antiperspirant/deodorant compositions of the invention comprise fragrances from about 0.01 to about 10 wt. %, relative to the total weight of the antiperspirant/deodorant composition. The antiperspirant/deodorant compositions of the invention comprise fragrances from about 0.1 to about 2 wt. %, based on the total weight of the antiperspirant/deodorant composition. The antiperspirant/deodorant compositions of the invention comprise fragrances in about 0.3 wt. %, based on the total weight of the antiperspirant/deodorant composition.

The pH of the antiperspirant/deodorant composition can be in the range of 7 to 11, or 7.5 to 10.5, or 8 to 10, or 8.5 to 9.5, or 9 to 9.5 or 9 to 10.

Some ingredients used in the compositions of the invention can have several properties, for instance polyethylene glycol can have humectant properties as well as thickening properties.

The antiperspirant/deodorant compositions may comprise about 5 to about 30 wt. % of one or more humectant(s), the one or more humectant(s) comprising glycerin; about 1 to about 10 wt. % of one or more nonionic surfactant(s) comprising a fatty alcohol ethoxylate; about 1 to about 10 wt. % of one or more thickener(s) comprising hydroxypropyl methylcellulose, polyethylene glycol, polyacrylic acid, cross-linked homopolymer of acrylic acid, acrylates of $C_{10-30}$ alkyl acrylate crosspolymer, or a combination of two or more thereof; optionally, about 0.1 to about 10 wt. % of preservatives, about 0.1 to about 5 wt. % of alpha hydroxy acids, optionally about 0.01 to about 10 wt. % of fragrances, and a carrier comprising water, wherein all weight percentages are based on the total weight of the antiperspirant/deodorant composition. The antiperspirant/deodorant compositions may comprise about 15 to about 18 wt. % of humectants, about 1 to about 10 wt. % of nonionic surfactants, about 1 to about 5 wt. % of thickeners, optionally about 0.1 to about 2 wt. % of preservatives, about 0.05 to about 0.15 wt. % of alpha hydroxy acids, optionally about 0.1 to about 2 wt. % of fragrances, and carriers, wherein all weight percentages are based on the total weight of the antiperspirant/deodorant composition. The antiperspirant/deodorant compositions may comprise about 10 to about 15 wt. % of humectants, about 1 to about 5 wt. % of thickeners, about 1 to about 10 wt. % of nonionic surfactants, about 0.1 to about 2 wt. % of preservatives, about 1 to about 5 wt. % of antioxidants, about 2 to about 5 wt. % of surfactants, about 0.1 to about 2 wt. % of fragrances and carriers, wherein all weight percentages are based on the total weight of the antiperspirant/deodorant composition. The antiperspirant/deodorant compositions of the invention comprise about 10 to about 15 wt. % of humectants, about 1 to about 5 wt. % of thickeners, about 0.1 to about 2 wt. % of preservatives, about 2 to about 5 wt. % of surfactants, about 0.1 to about 2 wt. % of fragrances and carriers, wherein all weight percentages are based on the total weight of the antiperspirant/deodorant composition.

The antiperspirant/deodorant compositions of the invention comprise about 18 wt. % of humectants, about 1.35 wt. % of thickeners, about 0.3 wt. % of preservatives, about 0.15 wt. % of alpha hydroxy acids, and about 0.3 wt. % of fragrances, wherein all weight percentages are based on the total weight of the antiperspirant/deodorant composition. The antiperspirant/deodorant compositions of the invention comprise about 15% by weight of humectants, about 3.75 wt. % of thickeners, about 0.3 wt. % of preservatives, about 0.15 wt. % of alpha hydroxy acids and about 0.3% by weight of fragrances wherein all weight percentages are based on the total weight of the antiperspirant/deodorant composition.

In one embodiment, the antiperspirant/deodorant composition comprises humectants, thickeners, preservatives, alpha hydroxy acids, and carriers. In one embodiment, the antiperspirant/deodorant composition is free-from aluminum salts. In one embodiment, the antiperspirant/deodorant composition is formulated as a stick, a gel, a cream, a glide, a roll-on, a soft solid, wipes, pads, towelette, soft solid, a powder, a liquid, an emulsion, a suspension, a dispersion, an aerosol, or a spray. In one embodiment, the antiperspirant/deodorant composition is formulated as a roll-on. In one embodiment, the antiperspirant/deodorant composition is formulated as a stick. In one embodiment, the humectants are selected from vegetable refined glycerin, non-crystal sorbitol, xylitol, propylene glycol, polyethylene glycol, polyoxyethylenes, ethylene glycol, diethylene glycol, hexylene glycol, butylene glycol and combinations thereof. In one embodiment, the humectants comprise vegetable refined glycerin. In one embodiment, the humectants comprise polyethylene glycol. In one embodiment, the humectants are comprised from about 5 to about 30 wt. % or from about 10 to about 20 wt. %, based on the total weight of the antiperspirant/deodorant composition. In one embodiment, the thickeners are selected from hydroxypropyl methylcellulose, polyethylene glycol, polyacrylic acid, cross-linked homopolymer of acrylic acid, acrylates of $C_{10-30}$ alkyl acrylate crosspolymer and combinations thereof. In one embodiment, the thickeners are selected from hydroxypropyl methylcellulose, polyethylene glycol, and combinations thereof. In one embodiment, the thickeners are comprised from about 1 to about 10 wt. %, based on the total weight of the antiperspirant/deodorant composition. In one embodiment, the preservatives are selected from caprylyl glycol, phenoxyethanol, butylated hydroxytoluene, ethylenediaminetetraacetic acid, ethylhexylglycerin, citric acid, benzoic acid, and combinations thereof. In one embodiment, the preservatives are comprised from about 0.1 to about 10 wt. %, based on the total weight of the antiperspirant/deodorant composition.

In one embodiment, the alpha hydroxy acids are selected from mandelic acid, glycolic acid, citric acid, lactic acid, malic acid, tartaric acid, phytic acid, hydroxycaprylic acid, hydroxycapric acid and combinations thereof. In one embodiment, the alpha hydroxy acids are comprised from about 0.1 to about 5 wt. %, based on the total weight of the antiperspirant/deodorant composition. In one embodiment, the antiperspirant/deodorant composition further comprises plant-based oils, antioxidants, antibacterial agents, fragrances, deodorizing agents, skin soothing agents, vitamins, pH adjusters, polymers, or combinations thereof. In one embodiment, the antiperspirant/deodorant composition comprises about 5 to about 30 wt. % of humectants, about 1 to about 10 wt. % of thickeners, about 0.01 to about 10 wt. % of preservatives, about 0.1 to about 5 wt. % of alpha hydroxy acids, and about 0.01 to about 10 wt. % of fragrances, based on the total weight of the composition. In one embodiment, the invention provides a method of reducing sweat in a subject in need thereof, comprising applying the antiperspirant/deodorant composition of the invention, to the axillary region of the subject in need thereof. In one embodiment, the invention provides a method of reducing sweat of at least 20%. In one embodiment, the invention provides a method of reducing malodor in the axillary region caused by excessive sweat, comprising applying the antiperspirant/deodorant composition of the invention to the axillary region of a subject in need thereof. In one embodiment, the antiperspirant/deodorant composition comprises about 5 to about 30 wt. % of vegetable refined glycerin. In one embodiment, the antiperspirant/deodorant composition comprises about 5 to about 10 wt. % of vegetable refined glycerin, based on the total weight of the antiperspirant/deodorant composition. In one embodiment, the antiperspirant/deodorant composition comprises about 10 to about 15 wt. % of vegetable refined glycerin, based on the total weight of the antiperspirant/deodorant composition. In one embodiment, the antiperspirant/deodorant composition comprises about 1 to about 10 wt. % of hydroxypropyl methylcellulose, based on the total weight of the antiperspirant/deodorant composition. In one embodiment, the antiperspirant/deodorant composition comprises about 1 to about 3 wt. % of hydroxypropyl methylcellulose, based on the total weight of the antiperspirant/deodorant composition. In one embodiment, the antiperspirant/deodorant composition comprises about 1 to about 1.5 wt. % of hydroxypropyl methylcellulose, based on the total weight of the antiperspirant/deodorant composition. In one embodiment, the antiperspirant/deodorant composition comprises about 1 to about 10 wt. % of polyethylene glycol 600, based on the total weight of the antiperspirant/deodorant composition. In one embodiment, the antiperspirant/deodorant composition comprises about 1 to about 3 wt. % of polyethylene glycol 600, based on the total weight of the antiperspirant/deodorant composition. In one embodiment, the antiperspirant/deodorant composition comprises about 0.1 to about 10 wt. % of caprylyl glycol, based on the total weight of the antiperspirant/deodorant composition. In one embodiment, the antiperspirant/deodorant composition comprises about 0.2 to about 0.4 wt. % by weight of caprylyl glycol, based on the total weight of the antiperspirant/deodorant composition. In one embodiment, the antiperspirant/deodorant composition comprises about 0.05 to about 2 wt. % of lactic acid, based on the total weight of the antiperspirant/deodorant composition. In one embodiment, the antiperspirant/deodorant composition comprises about 0.05 to about 0.1 wt. % of lactic acid, based on the total weight of the antiperspirant/deodorant composition. In one embodiment, the antiperspirant/deodorant composition comprises about 0.1 to about 0.15 wt. % of lactic acid, based on the total weight of the antiperspirant/deodorant composition. The embodiments of antiperspirant/deodorant compositions described herein are free-from aluminum salts used as antiperspirant actives.

In other aspects, the invention provides a method of reducing sweat comprising applying the antiperspirant/deodorant composition as disclosed hereinabove to an axillary area of a person, wherein the antiperspirant/deodorant composition reduces sweat. Since antiperspirant/deodorant products are considered over-the-counter the Food and Drug Administration has regulated this kind of products. An antiperspirant product must reduce sweat production by at least 20% over a 24-hour period after application. In other embodiments, the invention provides a method of reducing sweat from about 10 to about 40%, about 15 to about 20%, about 20 to about 25%, about 25 to about 30%, about 30 to about 35%, about 35 to about 40%, e.g., over a 24-hour period after application. In some embodiments, the invention provides a method of reducing sweat of about 20%. In some embodiments, the invention provides a method of reducing sweat of about 30%. In some embodiments, the invention provides a method of reducing sweat of at least about 20%. In some embodiments, the invention provides a method of reducing sweat of at least about 30%. The aluminum free antiperspirant/deodorant compositions of the invention were formulated as roll-on and tested with the back screening methodology. The effectiveness of the aluminum free roll-on formulations of the invention was compared to the effectiveness of commercial antiperspirants which are aluminum free.

A non-limiting, exemplary aluminum free antiperspirant/deodorant roll-on formulations may comprise ingredients tabulated in Table 1.

TABLE 1

Aluminum free antiperspirant/deodorant roll-on formulations

| | INGREDIENTS | WEIGHT (%) |
|---|---|---|
| 1 | Hygroscopic agents/humectants (e.g. vegetable refined glycerin, non crystal sorbitol, xylitol or low molecular weight polyethylene glycols, polyoxyethylenes) | 5 to 30 |
| 2 | Thickeners (e.g. hydroxypropyl methylcellulose, polyethylene glycol, carbomer) | 1 to 10 |
| 3 | Nonionic Surfactant (e.g., alcohol ethoxylate) | 0.5 to 10 |
| 4 | Anti-foam agents/preservatives (e.g. caprylyl glycol, phenoxyethanol, butylated hydroxytoluene, ethylenediaminetetraacetic acid, ethylhexylglycerin, citric acid, benzoic acid, sodium benzoate) | 0.1 to 10 |
| 5 | Alpha hydroxy acids (e.g., mandelic acid, glycolic acid, citric acid, lactic acid, malic acid, tartaric acid, phytic acid, hydroxycaprylic acid, hydroxycapric acid) | 0.05 to 2 |
| 6 | Other ingredients (e.g., fragrance, antibacterials, surfactants, plant based oils, antioxidants, antibacterial agents, deodorizing agents, skin soothing agents, vitamins, pH adjusters, polymers) | 0.01 to 10 |
| 7 | Carriers (e.g., demineralized water) | qs* |

*q.s. means the amount which is enough to make 100

Method of Preparation

The thickeners were added with slow stirring to demineralized water heated at 70-75° C. Once the addition was completed, the stirring speed was increased. The temperature was decreased to 55-60° C. and the humectants were added to support the temperature decrease. When the blend reached 55-60° C., the preservatives and alpha hydroxy acids were added. The blend was continuously stirred for another 10 minutes, allowing the temperature to reach 40-45° C. If the composition comprised additional ingredients (plant based oils, antioxidants, surfactants, antibacterial agents, deodorizing agents, skin soothing agents, vitamins, pH adjusters, polymers, or combinations thereof) these were added once the temperature was within 40-45° C. The product was stirred for an additional 20 minutes before filling the dispensing recipients.

EXAMPLES

The following examples are for illustrative purposes only and are not intended, nor should they be construed as limiting the invention in any manner. Those skilled in the art will appreciate that variations and modifications of the following examples can be made without exceeding the spirit or scope of the invention.

Example 1. Back Screening Methodology

Back screening tests are a common tool to perform preliminary studies to evaluate the performance of antiperspirant formulations. The diffusion rate into the skin of the vegetable refined glycerin is dependent on the presence of hydroxypropyl methylcellulose and/or polyethylene glycol. Therefore, the antiperspirant/deodorant testing formulations of the invention were evaluated according to this methodology. About fifty study subjects were recruited. Basal sweat was collected from twelve different areas of the skin on the back of the subjects. Twelve equal areas of the skin to be tested were selected and cleansed with soap and water. Pieces of fabric were weighted and applied to these skin areas. The sweat was induced by the increase in temperature with the help of a hot room. After 80 minutes, the pieces of fabric with sweat were removed and the initial and final difference in weight was registered. After determining the basal sweat measurements, the roll-on antiperspirant/deodorant testing formulations of the invention were evaluated. The skin areas were cleansed with soap and water. The roll-on samples were applied once a day on the skin and covered with pieces of fabric.

This procedure was repeated during three consecutive days. 24 hours after the third application, sweat was collected according to the basal sweat measurement procedure. One skin area remained untreated to provide estimates of sweat reduction.

Example 2. Sweat Reduction Evaluation for the Aluminum Free Roll-On Antiperspirant/Deodorant Formulations of the Invention In order to evaluate the aluminum free roll-on antiperspirant/deodorant formulations of the invention, several formulations were prepared according to the method described above. The amount of humectant, specifically vegetable refined glycerin, was varied in the formulations. The prepared antiperspirant/deodorant formulations were tested in a clinical back screener test as described in Example 1.

The sweat reduction data for the formulations of the invention were compared to high efficacy commercial products, used as controls. These controls were selected because they display significant sweat reduction and have historically shown reproducibility and repeatability across previous independent back screening studies. The commercial products used as controls, are aluminum free. The formulations of the invention and the controls were tested in the same conditions.

TABLE 2

Sweat reduction data for commercial products

| | Commercial product | | | | |
|---|---|---|---|---|---|
| | A | B | C | D | E |
| sweat reduction [a] [%] | 15 | 14 | 1.4 | +10.8 | +11.7 |

[a] sweat reduction percentage refers to the amount of sweat unreleased to the skin surface in a treated site versus an untreated site of the skin.
A commercial product Deodorant Roll On
B commercial product Deodorant Roll On
C commercial product Deodorant Stick
D commercial product Deodorant Roll On
E commercial product Deodorant Stick

TABLE 3

Sweat reduction data for aluminum free roll-on antiperspirant/deodorant formulations of the invention

| | Sample | | | | | |
|---|---|---|---|---|---|---|
| Ingredients [a] [%] | Placebo | 1 | 2 | 3 | 4 | 5 |
| vegetable refined glycerin | 0 | 15 | 100 | 60 | 5 | 20 |
| hydroxypropyl methylcellulose | 1.35 | 1.35 | 0 | 0 | 1.35 | 0 |
| polyethylene glycol 600 | 2.5 | 2.5 | 0 | 0 | 2.5 | 0 |
| caprylyl glycol | 0.3 | 0.3 | 0 | 0 | 0.3 | 0 |
| lactic acid | 0.15 | 0.15 | 0 | 0 | 0.15 | 0 |
| alcohol ethoxylate | 5 | 2 | 0 | 0 | 2 | 0 |
| fragrance | 0.3 | 0.3 | 0 | 0 | 0.3 | 0 |
| demineralized water | qs | qs | 0 | 40 | qs | 80 |
| sweat reduction [b] [%] | 0 | 36.5 | 21.2 | 18.5 | 15.6 | 6.5 |

[a] according to Table 1;
[b] sweat reduction percentage refers to the amount of sweat unreleased to the skin surface in a treated site versus an untreated site of the skin.

What is claimed is:

1. A personal care composition comprising:
    a humectant comprising glycerin present in an amount of about 15 wt. % and polyethylene glycol present in an amount of about 2.5 wt. %, based on the total weight of the personal care composition;
    a preservative present in an amount of about 0.3 wt. %, based on the total weight of the personal care composition;
    a nonionic surfactant comprising an alcohol ethoxylate present in an amount of about 2 wt. %, based on the total weight of the personal care composition;
    a thickener comprising hydroxypropyl methylcellulose present in an amount of about 1.35 wt. %, based on the total weight of the personal care composition;
    an alpha hydroxy acid present in amount of about 0.15 wt. %, based on the total weight of the personal care composition; and
    water,
    wherein the personal care composition provides a sweat reduction of about 20% or more, and the personal care composition is free of aluminum salts; and
    wherein the term "about" when referring to a number means any number within a range of 10% of the number.

2. The personal care composition according to claim 1, wherein the personal care composition is free of zinc-based antiperspirant actives, iron-based antiperspirant actives, zirconium-based antiperspirant actives, titanium-based antiperspirant actives, and magnesium-based antiperspirant actives.

3. The personal care composition according to claim 1, wherein the personal care composition is formulated as a stick, a gel, a cream, a glide, a roll-on, a soft solid, wipes, pads, towelette, soft solid, a powder, a liquid, an emulsion, a suspension, a dispersion, an aerosol, or a spray.

4. The personal care composition according to claim 1, wherein the humectant further comprises sorbitol, xylitol, propylene glycol, polyoxyethylenes, ethylene glycol, diethylene glycol, hexylene glycol, butylene glycol and combinations thereof.

5. The personal care composition according to claim 1, wherein the humectant consists of glycerin and polyethylene glycol.

6. The personal care composition according to claim 1, wherein glycerin is present in an amount of 15% and poly glycol is present in an amount of 2.5 wt. %, based on the total weight of the personal care composition.

7. The personal care composition according to claim 1, wherein the thickener further comprises polyacrylic acid, cross-linked homopolymer of acrylic acid, acrylates of $C_{10-30}$ alkyl acrylate crosspolymer, and combinations of two or more thereof.

8. The personal care composition according to claim 1, wherein the thickener is hydroxypropyl methylcellulose present in an amount of 1.35 wt. %, based on the total weight of the personal care composition.

9. The personal care composition according to claim 1, wherein the preservative comprises caprylyl glycol, phenoxyethanol, butylated hydroxytoluene, ethylenediaminetetraacetic acid, ethylhexylglycerin, citric acid, benzoic acid, or a combination of two or more thereof.

10. The personal care composition according to claim 9, wherein the preservative is caprylyl glycol.

11. The personal care composition according to claim 1, wherein the alpha hydroxy acid is selected from mandelic acid, glycolic acid, citric acid, lactic acid, malic acid, tartaric acid, phytic acid, hydroxycaprylic acid, hydroxycapric acid and combinations thereof.

12. The personal care composition according to claim 1, wherein the alpha hydroxy acid is lactic acid.

13. The personal care composition according to claim 1, further comprising: a plant based oil, an antioxidant, an antibacterial agent, a fragrance, a deodorizing agent, a skin soothing agent, a vitamin, a pH adjuster, a polymer, or a combination of two or more thereof.

14. The personal care composition according to claim 1, comprising 15 wt. % of glycerin, 2.5 wt. % of polyethylene glycol, 0.3 wt. % of preservative 2 wt. % of alcohol ethoxylate, 1.35 wt. % of hydroxypropyl methylcellulose, and 0.15 wt. % of alphahydroxy acid, based on the total weight of the personal care composition.

15. The personal care composition according to claim 1, wherein the alcohol ethoxylate is selected from a polyoxyethylene stearyl ether; a polyoxyethylene ether; and a combination thereof.

16. The personal care composition according to claim 1, wherein the alcohol ethoxylate is selected from Ceteareth-2, Ceteareth-3, Ceteareth-4, Ceteareth-5, Ceteareth-6, Ceteareth-7, Ceteareth-8, Ceteareth-9, Ceteareth-10, Ceteareth-11, Ceteareth-12, Steareth-2, Steareth-4, Steareth-6, Steareth-7, Steareth-21, Steareth-10, Steareth-11, Steareth-13, Steareth-15, Steareth-20, and a combination of two or more thereof.

17. The personal care composition according to claim 1, wherein water is present in an amount of about 78.4 wt. %, based on the total weight of the personal care composition.

18. A method of reducing sweat of a subject in need thereof, the method comprising: applying the personal care composition according to claim 1, to the axillary region of the subject in need thereof.

19. The method according to claim 18, wherein the sweat reduction is of at least 20%.

20. A method of reducing malodor in the axillary region caused by excessive sweat, the method comprising: applying the personal care composition according to claim 1, to the axillary region of a subject in need thereof.

* * * * *